United States Patent [19]
Bahrmann et al.

[11] Patent Number: 5,847,200
[45] Date of Patent: Dec. 8, 1998

[54] SUBSTITUTED DIPHOSPHINES AND A PROCESS FOR THEIR PREPARATION

[75] Inventors: Helmut Bahrmann, Hamminkeln, Germany; Peter Lappe, Plano, Tex.; Thomas Muller, Dinslaken, Germany

[73] Assignee: Hoechst Aktiengesellschaft, Germany

[21] Appl. No.: 839,329

[22] Filed: Apr. 17, 1997

[30] Foreign Application Priority Data

May 15, 1996 [DE] Germany .................. 196 19 528.4

[51] Int. Cl.$^6$ ...................................... C07F 9/50
[52] U.S. Cl. .................. 562/35; 562/11; 562/13; 562/8; 562/20; 568/17
[58] Field of Search ................ 562/35, 11, 13, 562/8, 20; 568/17

[56] References Cited

U.S. PATENT DOCUMENTS 4,142,060  2/1979  Kuntz .
4,710,321  12/1987  Bahrmann .
4,716,250  12/1987  Abatjoglou et al. .
5,274,183  12/1993  Herman .
5,347,045  9/1994  Herrmann .

FOREIGN PATENT DOCUMENTS 0374615  6/1990  European Pat. Off. .
0571819  12/1993  European Pat. Off. .
0728762  9/1996  European Pat. Off. .
0358580  3/1990  France .

*Primary Examiner*—Gary Geist
*Assistant Examiner*—Jean F. Vollano
*Attorney, Agent, or Firm*—Bierman, Muserlian and Lucas

[57] ABSTRACT

New diphosphines in the form of ammonium carboxylates, sulfonates or phosphonates having a singly or multiply charged diphosphine anion and the corresponding number of ammonium cations as counter ions, and a process for their preparation useful as ligand in rhodium catalyst systems for hydroformylation of olefins.

13 Claims, No Drawings

SUBSTITUTED DIPHOSPHINES AND A PROCESS FOR THEIR PREPARATION

FIELD OF THE INVENTION

Phosphines are used in a wide variety of industrial processes. Of particular importance is their use as ligands for metal complex catalysts, preferably containing as a central atom, a metal of group VIII of the Periodic Table of the Elements plus, optionally, in addition to the phosphine ligands, further groups capable of complex formation.

STATE OF THE ART

The hydroformylation of olefins, which is widely carried out in the industry, is increasingly carried out in the presence of catalyst systems based on rhodium complexes containing tertiary phosphines or phosphites as ligands. Since these ligands are generally present in excess, the catalyst system comprises the complex and additional pure ligand. Since these catalyst systems are soluble in organic media, the hydroformylation is carried out in a homogenous phase.

To separate off the reaction products and recover the catalysts homogeneously dissolved in the reaction product, the reaction product is generally distilled from the reaction mixture. However, due to the heat-sensitivity of the aldehydes formed, this is only possible for the hydroformylation of lower olefins having up to about 8 carbon atoms in the molecule. The hydroformylation of long-chain olefins or olefinic compounds having functional groups results in the formation of high-boiling products which can no longer be satisfactorily separated from the catalyst by distillation. The thermal stressing of the material being distilled leads, as a result of thick oil formation, to considerable losses of the desired product and to losses of the catalyst as a result of decomposition of the complexes. This decisively reduces the economic attractiveness of the process.

It is known from EP-A-0 374,615 that organometallic complexes containing phosphorus (III) compounds as ligands can be separated off and recovered intact, i.e. without degradation of the catalytically active metal compound, from organic solvents using selective semipermeable polyamide separation membranes. The driving force for the separation process can be either a pressure difference (pressure filtration) or a concentration difference (dialysis). The process is particularly suitable for separating organometallic complexes and/or metal carbonyls containing phosphorus (III) compounds as ligands from organic solutions in which they have previously been employed as homogenous catalysts.

Rhodium complexes mentioned in EP-A-0 374,615 are $HRhCO[P(C_6H_5)_3]_3$, $RhCl[P(C_6H_5)_3]_3$ and compounds which contain as ligands alkylammonium or arylammonium salts of sulfonated or carboxylated triarylphosphines of the formula

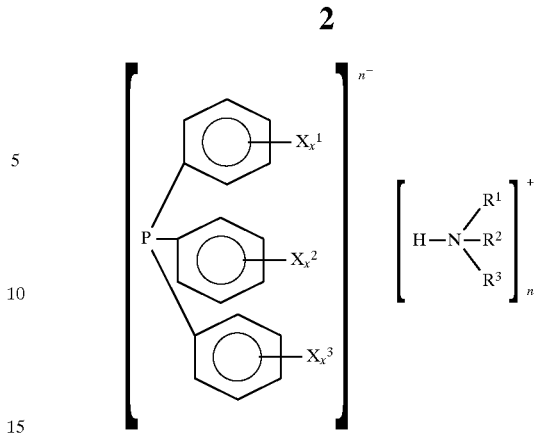

where X is sulfonate ($SO_3$) or carboxylate ($COO^-$), $X^1$, $X^2$ and $X^3$ are 0 or 1, $R^1$ and $R^2$ are individually alkyl of 4 to 12 carbon atoms, aryl of 6 to 12 carbon atoms or cycloalkyl of 6 to 12 carbon atoms and $R^1$ can also be hydrogen.

Such rhodium complexes containing alkylammonium or arylammonium salts of sulfonated or carboxylated triarylphosphines as ligands are used for the hydroformylation of olefinically unsaturated compounds in an homogenous phase, but they need to be stabilized by a large excess of free, uncomplexed ligands.

This high ligand excess leads to a high salt concentration in the hydroformylation mixture and this high salt concentration can have an unfavorable influence on the reaction of the olefin with carbon monoxide and hydrogen since it impairs the solubility of the reactants in the reaction mixture and, in addition, promotes foaming. In the case of a membrane filtration which can be carried out after the hydroformylation to separate the catalyst system from the reaction product, the high ligand excess, i.e. the high salt concentration, also has an adverse effect. On the one hand, it reduces the flow performance of the membrane filtration which can only be made up for by the use of very much larger membrane areas and on the other hand, it reduces the maximum degree to which the retentate can be concentrated. This leads, in the case of a recirculation of the catalyst-containing retentate to the hydroformylation reaction, to a reduction in the reactor volume available to the other reactants, an effect which, like the high membrane areas, leads to increased process costs and thus reduces the economic attractiveness of the process.

The high salt concentrations also interfere in the case of a work-up of the hydroformylation mixture by distillation since they lead to an increased proportion of salt-containing thick oil.

OBJECTS OF THE INVENTION

It is an object of the invention to provide new organophosphorus compounds which can be used as ligands in catalyst systems based on rhodium complexes for the hydroformylation of olefinically unsaturated compounds in a homogenous phase, lead to high activity and selectivity values in such a process and make possible a simple separation of the catalyst system from the hydroformylation product.

These and other objects and advantages of the invention will become obvious from the following detailed description.

THE INVENTION

The novel compounds of the invention have the formula

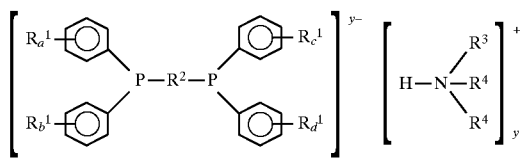

where $R^1$ is carboxylate (COO$^-$), sulfonate, (SO$_3^-$), phosphonate (PO$_3^{2-}$) and 2-aminoethanebisphosphonate [—NH—CH$_2$—CH(PO$_3^2$-)$_2$], $R^2$ is selected from the group consisting of a straight-chain alkylene of 1 to 8 carbon atoms, an oxygen-containing alkylene of 2 to 6 carbon atoms, cycloalkylene of 3 to 10 carbon atoms; y is an integer from 1 to 24 and a member of the formulae II, III, IV or V

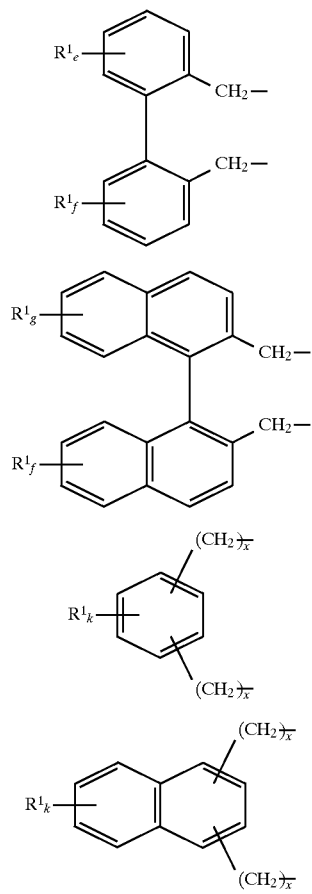

a, b, c, d, e, f, g, h, k and l are individually 0 or 1, where at least one of a, b, c, d, e, f, g, h, k or l has to be equal to 1, x are individually 0 to 1, $R^3$ and $R^4$ are individually selected from the group consisting of optionally substituted alkyl of 4 to 26 carbon atoms, aryl of 6 to 10 carbon atoms, cycloalkyl of 6 to 10 carbon atoms and benzyl and $R^3$ can also be hydrogen.

The compounds of Formula I are in the form of ammonium carboxylates, sulfonates or phosphonates having a singly or multiply charged diphosphine anion and the corresponding number of ammonium cations as counter ions. They are generally insoluble or only sparingly soluble in water. In contrast, they have a good to very good solubility in organic solvents and are therefore suitable for use in the organic phase.

In Formula I, $R^1$ is a carboxylate, sulfonate, phosphonate or 2-aminoethanebisphosphonate, preferably sulfonate.

$R^2$ is a straight-chain alkylene of 1 to 8 preferably 1 to 5 and more preferably 1 to 3, carbon atoms. $R^2$ can also be an oxygen-containing alkylene of 2 to 6, preferably 2 to 4 carbon atoms and more preferably 4 carbon atoms as represented by the formula —(CH$_2$)$_2$—O—(CH$_2$)$_2$—. $R^2$ can also be cycloalkylene of 3 to 10, preferably 6 to 10, carbon atoms or a member of formulae II, III, IV or V, preferably formula II.

In the formula I, II, III, IV and V, a, b, c, d, e, f, g, h, k and l are individually 0 or 1, where at least one of a, b, c, d, e, f, g, h, k or l has to be equal to 1. In compounds of formula I in which $R^2$ is formula II, the sum of a, b, c, d, e and f, which indicates the number of $R^1$ (s) is preferably 1 to 3. If $R^2$ is formula III, the sum of a, b, c, d, g and h is preferably 1 or 2. If $R^2$ is formulae IV or V, the sum of a, b, c, d and k or a, b, c, d and l is preferably 1 to 3. If $R^2$ is a straight-chain alkylene of 1 to 8 carbon atoms, an oxygen-containing alkylene of 2 to 6 carbon atoms or cycloalkylene of 3 to 10 carbon atoms, the sum of a, b, c and d is preferably 2 to 4.

In formulae IV and V, x is preferably 1 and the two methylene radicals are located in ortho positions relative to one another.

In formula I, $R^3$ and $R^4$ are individually alkyl of 4 to 26, preferably 18 to 22 carbon atoms, optionally substituted aryl of 6 to 10 carbon atoms, preferably phenyl, cycloalkyl of 6 to 10 carbon atoms, preferably cyclohexyl or benzyl. $R^3$ can also be hydrogen.

Thus, the ammonium cations [H—NR$^3$R$^4$R$^4$]$^+$ in formula I are derived from secondary or tertiary amines NR$^3$R$^4$R$^4$ containing a total of 8–78, preferably 12–72, more preferably, from 21 to 60 and most preferably, 36 to 54, carbon atoms in $R^3$ and $R^4$. The ammonium cations are preferably derived from di-2-ethylhexylamine, trioctylamine, triisooctylamine, triisononylamine, triisodecylamine, distearylamine, methyldistearylamine, tricetylamine or trieicosylamine.

As particularly suitable disphosphine anions in formula I, mentioned may be made of sulfonated disphosphine anions such as bis(disulfonatophenylphosphino) methane, 1,2-bis (disulfonatophenylphosphino) ethane, 1,3-bis (disulfonatophenylphosphino) propane, 1,4-bis (disulfonatophenylphosphino) butane, 1,5 -bis (disulfonatophenylphosphino) pentane, bis (diphenylphosphinomethyl) ether and bis (diphenylphosphinoethyl) ether.

The invention further provides a process for preparing the compounds of formula I where $R^1$ is sulfonate comprising reacting a secondary phosphine oxide of the formula

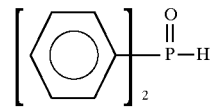

in the presence of a base with a dihalide of the formula

where $R^2$ is as defined for formula I and X is halogen, preferably chlorine or bromine, in the presence or absence of a solvent at −20° to 100° C. to obtain a diphosphine oxide of the formula

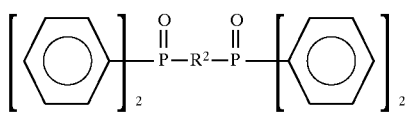

reducing the diphosphine oxide of formula VIII in the presence or absence of a solvent with a silane of the formula $HSiCl_mR^5_n$, wherein m is 2 or 3, n is 0 or 1 and m+n is equal to 3 and $R^5$ is methyl or phenyl, at 80°–160° C. to obtain a diphosphine of the formula

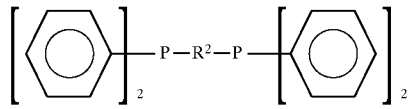

and sulfonating the diphosphine of formula IX at 0° to 50° C. using oleum, diluting the sulfonation mixture with water and adding the water-insoluble amine $NNR^3R^4R^4$, from which the ammonium cation $[H—NR^3R^4R^4]^+$ in formula I is derived dissolved in a water-insoluble organic solvent.

The phosphine oxide of formula VI is reacted with the dihalide $X—R^2—X$ in a molar ratio of 1:(2–3), preferably 1:2.5. This reaction is carried out in the presence of a base to bind the hydrogen halide, HCl or HBr, liberated in this reaction. The base used can be a compound MeH, where Me is Li, Na or K, or a compound LiR', where R' is alkyl of 1 to 4 carbon atoms or phenyl. It is also possible to use mixtures of the above-mentioned bases.

The diphosphine oxide of formula VIII is subsequently reduced in the presence or absence of a solvent with a silane of the formula $HSiCl_mR^5_n$, where m and n are as defined above, particularly with a silane of the formula $HSiCl_2R^5$, where $R^5$ is methyl or phenyl at a temperature of 100° to 150° C. This reduction can also be carried out at higher or lower temperatures, but in many cases, the temperature range of 100° to 150° C. has been found to be convenient and satisfactory. The reduction of the diphosphine oxide of formula VIII is preferably carried out in the presence of a solvent. For this purpose, use is usually made of an organic solvent which is inert under the conditions of the reduction, e.g. acetonitrile, toluene or xylene. After the reduction of the diphosphine oxide of formula VIII, the diphosphine of formula IX is obtained.

To introduce sulfonic acid groups into phenyl and any binaphthyl present in $R^2$ of the diphosphine of the formula IX, the diphosphine is treated with excess sulfur trioxide in the form of oleum as the sulfonating agent. Factors which are decisive for the achievable degree of sulfonation are, particularly the $SO_3$ concentration in the oleum, the reaction temperature and the reaction time. The parameters mentioned have an influence on one another.

Use is usually made of oleum containing 10 to 65% or more by weight of sulfur trioxide. Oleum containing 25% by weight of sulfur trioxide has been found to be particularly useful. The sulfonating agent is to be used in excess, based on the diphosphine. From 5 to 80 moles, preferably from 15 to 30 moles, of $SO_3$ are advantageously used per mole of diphosphine. Oleum containing free $SO_3$ in a higher concentration, i.e. a proportion of from about 40 to 65% and more by weight is used in the case of diphosphines of formula IX in which $R^2$ is a straight-chain alkylene of 1 to 8 carbon atoms, an oxygen-containing alkylene of 2 to 6 carbon atoms or cycloalkylene of 3 to 10 carbon atoms. This gives products containing 2 to 4 and possibly more sulfonate groups. Concentrations of free $SO_3$ in oleum which are lower than about 40% by weight are used in the case of diphosphines of formula IX in which $R^2$ is formulae II, III, IV or V, giving lower sulfonated products containing 1 to 3 sulfonate groups.

The reaction temperature is 0° to 50° C, preferably 10° to 40° C. In principal, it is also possible to employ higher temperatures, but they promote the oxidation of the diphosphines to phosphine oxides significantly more strongly than the sulfonation, so that overall, the yield of sulfonated diphosphines decreases. For this reason, it is also not advisable to compensate for lower concentrations of free $SO_3$ by increasing the reaction temperature.

In contrast, the degree of sulfonation of the diphosphine can be successfully influenced by the reaction time. Longer reaction times lead to more highly sulfonated compounds than do shorter times. The most desirable degree of sulfonation depends on the bulkiness of the resulting ligands. In the case of simple compounds of formula I wherein $R^2$ is, for example, a straight-chain alkylene of 1 to 8 carbon atoms, a relatively high degree of sulfonation of 2 to 4 is sought. In contrast, in the case of stearically more demanding compounds of formula I, e.g. those having $R^2$ of formula III, only a relatively low degree of sulfonation of 1 to 2 is sought. In general, the reaction in the temperature ranges mentioned takes from 1 to 80 hours, preferably from 6 to 72 hours and more preferably 10 to 60 hours.

This time frame applies in particular when using oleum containing about 40% and more by weight of free sulfur trioxide. Oleum of lower concentration leads, even in the case of long reaction times, only to partially sulfonated compounds. In addition, the increasing formation of oxidation products cannot be completely avoided. Advantageously, the degree of sulfonation is also controlled via the reaction time.

As solvent for the starting compound to be sulfonated, concentrated sulfuric acid has been found to be useful. This solution can be introduced a little at a time into oleum or oleum can be added a little at a time. It is advisable to stir the reaction mixture vigorously, to cool it well and to combine the reactants slowly and in small portions so that the heat of reaction can be dissipated easily. This prevents the sulfonation from proceeding in an uncontrolled manner, and instead, the sulfonate groups are introduced successively into the phenyls and any binaphthyls. In addition, oxidation of the phosphorus compound is effectively suppressed.

After addition of the total amount of sulfonating agent or diphosphine, a further reaction can be carried out at room temperature, i.e. at from about 20° to 25° C., and essentially without external cooling. However, it is advantageous to stir the reaction mixture even at this stage to uniformly distribute any heat of reaction still being evolved and to be able to dissipate it without delay.

Subsequent to the sulfonation, the reaction solution is hydrolyzed. In this process step, care has to be taken to ensure that a temperature of about 30° C. is not exceeded and it is advantageous to maintain temperatures in the range of 15° to 25° C. It is, therefore, advisable to carefully pour the reaction mixture onto ice or to carry out the hydrolysis using ice or ice water and to provide intense external cooling. It is recommended here that sufficient water to dilute the sulfuric acid present to 0.5–50% by weight, preferably 25–35% by weight, be added.

To the diluted solution comprising essentially the sulfonation mixture of the diphosphine and sulfuric acid, there is added the water-insoluble amine from which the ammonium cation $[H—NR^3R^4R^4]^+$ in formula I is derived, dissolved in a water-insoluble organic solvent. The amine solution contains 0.5–35% by weight, preferably 10–30% by weight and more preferably 15–25% by weight, of amine.

0.5–1.5 mole, preferably 0.8–1.2 mole, of amine is used per equivalent of sulfonic acid groups. The use of excess amine ensures that only small yield losses occur. Although an even higher amine excess is possible, it does not lead to a further improvement in the yield. Amines used are the secondary or tertiary amines mentioned above.

Solvents used for the amine are aliphatic or aromatic hydrocarbons or hydrocarbon mixtures, e.g. toluene or kerosine-like hydrocarbon fractions, or else $C_4$–$C_{20}$-alcohols or $C_8$–$C_{20}$-ethers.

Due to the incorporation of two trivalent phosphorus atoms in the molecule, the compounds of formula I are very useful as chelating ligands. In particular, they have excellent utility as constituents of catalyst systems, e.g. for the hydroformylation of olefinically unsaturated compounds. This is the subject matter of U.S. patent application Ser. No. 839,330 filed on the same day as the present patent application.

In the following examples, there are described various preferred embodiments to illustrate the invention. However, it should be understood that the invention is not intended to be limited to the specific embodiments.

EXAMPLES

Preparation of the distearylammonium salt of 1,3-bis(di-m-sulfonatophenylphosphino)propane (ligand 1).

1,3-bis(diphenylphosphino)propane was sulfonated with oleum and the reaction mixture obtained was hydrolyzed by addition of cold water. The P(III) concentration of the hydrolysis mixture was 42 mmol/kg and 460.6 g of the hydrolysis mixture were placed in a stirred flask. Then, a solution of 96.6 g of distearylamine in 386 g of toluene was added thereto and the mixture was stirred for 60 minutes at 50° C. After stirring had been stopped, the aqueous phase containing sulfuric acid was separated off. The pH was adjusted to 2.6 by addition of 5% strength aqueous sodium hydroxide solution at 45° C. and the mixture was allowed to react further for 20 minutes. To improve phase separation, 129 g of toluene were then added and after 30 minutes, 662.9 g of an organic phase containing the ammonium salt of ligand 1 were obtained. The P(III) transfer into the organic phase was calculated as 78.9%, based on the P(III) used.

What we claim is:

1. A water-insoluble compound of the formula

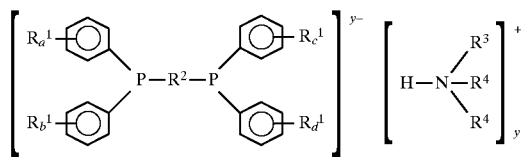

wherein $R^1$ is selected from the group consisting of carboxylate ($COO^-$) sulfonate ($SO_3^-$), phosphonate ($PO_3^{2-}$) and 2-aminoethanebisphosphonate, $R^2$ is selected from the group consisting of straight-chain alkylene of 1 to 8 carbon atoms, an oxygen-containing alkylene of 2 to 6 carbon atoms, cycloalkylene of 3 to 10 carbon atoms and a member of the formulae II, III, IV or V

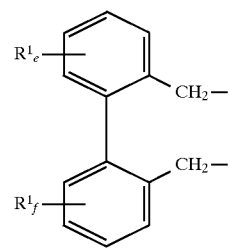

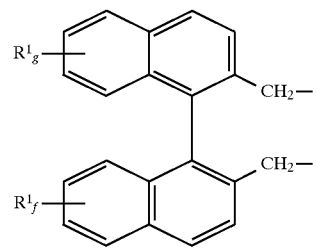

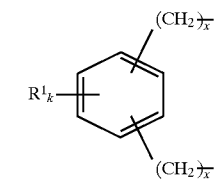

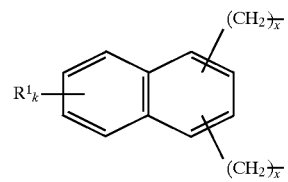

a, b, c, d, e, f, g, h, k and l are individually 0 or 1, where at least one of a, b, c, d, e, f, g, h, k or l has to be equal to 1, x(s) are individually 0 to 1, y is an integer of 1 to 24, $R^3$ and $R^4$ are individually selected from the group consisting of optionally substituted alkyl of 4 to 26 carbon atoms, aryl of 6 to 10 carbon atoms, cycloalkyl of 6 to 10 carbon atoms and benzyl and $R^3$ can also be hydrogen.

2. A water-soluble compound of claim 1, wherein $R^1$ is sulfonate.

3. A water-soluble compound of claim 1 wherein $R^2$ is selected from the group consisting of a straight-chain alkylene of 1 to 5 carbon atoms, an oxygen-containing alkylene of 2 to 4 carbon atoms, cycloalkylene of 6 to 10 carbon atoms and a member of formula II.

4. A water-soluble compound of claim 1 wherein the sum of a, b, c, d, e and f in compounds of formula I in which $R^2$ is formula II is 1 to 3.

5. A water-soluble compound of claim 1 wherein the sum of a, b, c, d, g and h in compounds of formula I in which $R^2$ is formula III is 1 to 2.

6. A water-soluble compound of claim 1 wherein the sum of a, b, c, d and k or a, b, c, d and l in compounds of formula I in which $R_2$ is formula IV or V is 1 to 3.

7. A water-soluble compound of claim 1 wherein the sum of a, b, c and d in compounds of formula I in which $R^2$ is selected from the group consisting of straight-chain alkylene of 1 to 8 carbon atoms, an oxygen-containing alkylene of 2 to 6 carbon atoms and cycloalkylene of 3 to 10 carbon atoms is 2 to 4.

8. A water-soluble compound of claim 1 wherein the ammonium cations $[H-NR^3R^4R^4]^+$ in formula I are derived from secondary or tertiary amines $NR^3R^4R^4$, where $R^3$ and $R^4$ are individually selected from the group consisting of alkyl of 18 to 22 carbon atoms, optionally substituted phenyl and cyclohexyl and $R^3$ can also be hydrogen.

9. A water-soluble compound of claim 8, wherein the ammonium cations $[H—NR^3R^4R^4]^+$ contain a total of 8 to 78 carbon atoms in $R^3$ and $R^4$.

10. A water-soluble compound of claim 8, wherein the ammonium $[H—NR^3R^4R^4]^+$ cations are selected from the group consisting of di-2-ethylhexylamine, tri-n-octylamine, triisooctylamine, triisonoylamine, triisodecylamine, distearylamine, methyldistearylamine, tricetylamine and trieicosylamine.

11. A water-soluble process for preparing a compound of claim 1, where $R^1$ is sulfonate comprises reacting a secondary phosphine oxide of the formula

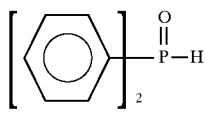   VI in the presence of a base with a dihalide of the formula

   VII where $R^2$ is as defined in claim 1 and X is halogen in the presence or absence of a solvent at $-20°$ to $100°$ C. to obtain a diphosphine oxide of the formula

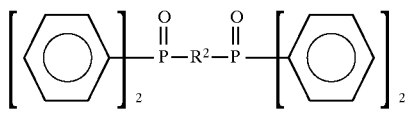   VIII reducing the diphosphine oxide of formula VIII in the presence or absence of a solvent with a silane of the formula $HSiCl_mR^5_n$, where m is 2 or 3, n is 0 or 1, m+n is equal to 3 and $R^5$ is methyl or phenyl at $80°–160°$ C. to obtain a diphosphine of the formula

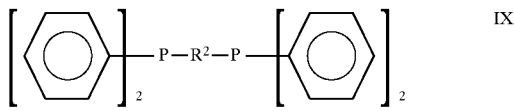   IX and sulfonating the diphosphine of formula IX at $0°$ to $50°$ C. using oleum, diluting the sulfonation mixture with water and adding the water-insoluble amine $NR^3R^4R^4$, from which the ammonium cation $[H—NR^3R^4R^4]^+$ in formula I is derived, dissolved in a water-insoluble organic solvent.

12. The process of claim 11, wherein the sulfonation of the diphosphine of formula IX is carried out at $0°–50°$ C., for 1–80 hours, the sulfonation is carried out using oleum containing 10–65% by weight of sulfur trioxide and from 5 to 80 moles of sulfur trioxide are used per mole of diphosphine of formula IX.

13. The process of claim 11 wherein in the addition of the water-insoluble amine $NR^3R^4R^4$ dissolved in a water-insoluble organic solvent, 0.5–1.5 mole of amine $NR^3R^4R^4$ is used per equivalent of sulfonic acid group and the solvent used for the amine is selected from the group consisting of toluene, aliphatic hydrocarbons, $C_4$–$C_{20}$ alcohols and $C_8$–$C_{20}$-ethers.

* * * * *